US009463337B2

(12) United States Patent
Koshti et al.

(10) Patent No.: US 9,463,337 B2
(45) Date of Patent: Oct. 11, 2016

(54) MULTIFUNCTIONAL HAIR COLOR PROTECTOR

(71) Applicant: GALAXY SURFACTANTS LTD., Maharashtra (IN)

(72) Inventors: Nirmal Koshti, Upper Saddle River, NJ (US); Pooja Vaidya Kshirsagar, Nagpur (IN); Bhagyesh Sawant, Mumbai (IN)

(73) Assignee: GALAXY SURFACTANTS LTD, Maharashtra (IN)

( * ) Notice: Subject to any disclaimer, the term of this patent is extended or adjusted under 35 U.S.C. 154(b) by 343 days.

(21) Appl. No.: 13/849,912

(22) Filed: Mar. 25, 2013

(65) Prior Publication Data
US 2014/0199254 A1 Jul. 17, 2014

(30) Foreign Application Priority Data
Jan. 17, 2013 (IN) ............................. 162/MUM/2013

(51) Int. Cl.
| *A61K 8/42* | (2006.01) |
| *A61Q 5/12* | (2006.01) |
| *C07C 211/63* | (2006.01) |
| *C07C 231/12* | (2006.01) |
| *A61Q 5/00* | (2006.01) |
| *A61Q 17/04* | (2006.01) |
| *A61Q 5/02* | (2006.01) |

(52) U.S. Cl.
CPC . *A61Q 5/12* (2013.01); *A61K 8/42* (2013.01); *A61Q 5/002* (2013.01); *A61Q 5/004* (2013.01); *A61Q 17/04* (2013.01); *C07C 211/63* (2013.01); *C07C 231/12* (2013.01); *A61K 2800/48* (2013.01); *A61Q 5/02* (2013.01)

(58) Field of Classification Search
CPC ...................................................... C07C 211/63
See application file for complete search history.

(56) References Cited

U.S. PATENT DOCUMENTS

| 5,427,773 A | 6/1995 | Chaudhuri et al. |
| 5,601,811 A | 2/1997 | Gallagher et al. |
| 6,426,435 B1 | 7/2002 | Koshti et al. |
| 6,531,628 B1 | 3/2003 | Koshti et al. |
| 6,613,340 B2 | 9/2003 | Koshti et al. |
| 7,147,866 B2 | 12/2006 | Koshti et al. |
| 7,202,204 B2 | 4/2007 | Pereira et al. |
| 7,205,436 B2 | 4/2007 | Koshti et al. |

OTHER PUBLICATIONS

Cullum, D.C., "Introduction to Surfactant Analysis", Chapman & Hall; 1994 (8 pp).
"Ingredients Trends in Hair Care: Meeting the Needs of the 21st Century Customer", Euromonitor International, Apr. 2011 (36 pp.).
Milwidsky, B.M., et al. "Detergent Analysis: A Handbook for Cost-effective Quality Control", John Wiley & Sons, Inc., New York, 1982 (5 pp).

*Primary Examiner* — Benjamin Packard
(74) *Attorney, Agent, or Firm* — Cantor Colburn LLP

(57) ABSTRACT

This invention relates to the synthesis of a multifunctional hair color protector, p-methoxy cinnamidoproyl dimethyl behenyl ammonium chloride of Formula I and the compositions containing the same for hair care.

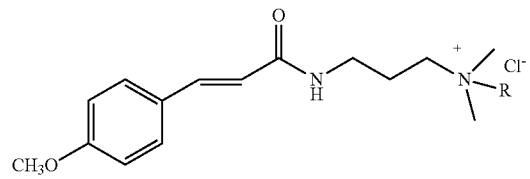

2 Claims, 3 Drawing Sheets

MULTIFUNCTIONAL HAIR COLOR PROTECTOR

CROSS REFERENCE TO RELATED APPLICATION

Figure 1:
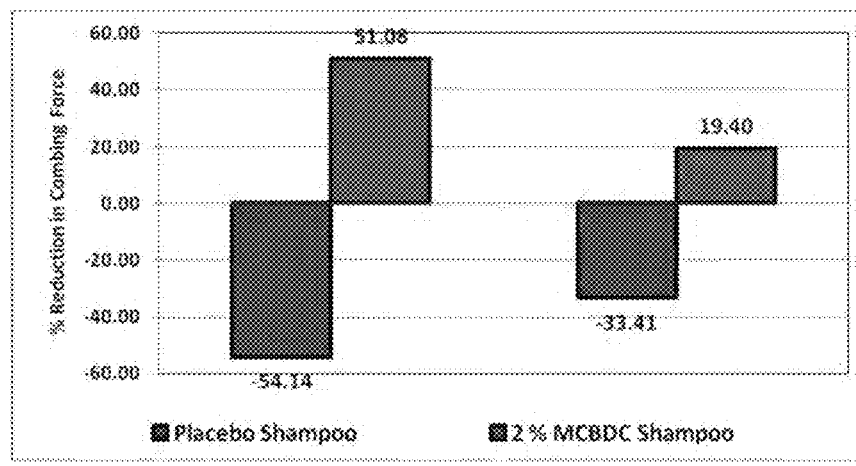

The present invention claims priority under 35 U.S.C. §119 to Indian Application No. 162/MUM/2013 filed Jan. 17, 2013, the entire content of which is incorporated herein by reference.

FIELD OF INVENTION

The invention relates to both prevention of damage and repairing of damaged hair as a result of light, heat treatment and the chemical treatment. More particularly, it relates to a novel aqueous process of preparing multifunctional substantive hair conditioner that protects the applied hair color and further the use of the said multifunctional substantive hair conditioner in hair care formulations.

BACKGROUND AND PRIOR ART

Coloring hair is an increasing global trend. The colors that are applied on hair, by nature of their chemical structures, are susceptible to the damaging effect of light and heat. This results in the appreciable degree of fading of the applied color. Curling, straightening, bleaching and coloring of hair causes damage substantially since these procedures involve intense heat and chemical treatment. Some of the procedures involve breaking down of covalent bonds by chemical treatments involving very harsh chemicals like sodium hydroxide or strong oxidizing agents like hydrogen peroxide. This kind of chemical assault coupled with damaging effect of solar radiation makes hair rough, brittle, dull and lifeless. The damage due to heat, chemicals and UV light to hair cuticles is easily felt and seen. A close examination of products available in market reveals that shampoos and rinse-off conditioners that have been specifically designed for colored hair contain mostly water-soluble UV absorbers such as benzophenone-4 (B-4) or phenyl benzimidazole sulphonic acid (PBSA). Occasionally, one sees use of oil-soluble UV absorbers like octyl methoxy cinnamate in conjunction with water-soluble UV absorbers in hair care formulations that are targeted for color protection. However, via rinse-off applications the deposition of water-soluble UV absorber is too insignificant to protect hair or the applied hair color from the damaging effect of sunlight. To overcome this problem water-soluble cationic UV absorbers (U.S. Pat. No. 5,601,811) have been developed. Croda's Incroquat UV-283, cinnamido propyl trimethyl ammonium chloride is one such quaternary UV absorber. Another U.S. Pat. No. 6,426,435 reports water-soluble quaternary UV absorbers, bis-quaternary salts of cinnamidoalkylamines. Though these are quaternary (cationic) molecules and do have higher substantivity/affinity to hair tresses compared to nonquaternized UV absorbers, their extremely high water-solubility restricts the extent of deposition on hair through rinse-off of formulation. Yet another U.S. Pat. No. 6,531,628 teaches the use of water-soluble 2-hydroxy sulphobetaine moiety attached to UV absorbing chromophore. Whether the betaine type or the quaternary ammonium type, both classes exhibit better substantivity than simple salts of water-soluble sunscreen sulphonic acids (B-4 or PBSA), however, the extremely high water-solubility works against any meaningful deposition on hair surface. This problem, in part, was overcome by water-insoluble quaternized UV absorbers that have UV absorbing moiety attached to lauryl group (C-12) through a quaternary nitrogen center. The commercial products known as Escalol HP 610 by Ashland Chemicals and Galaxy TosyQuat by Galaxy Surfactants Ltd. U.S. Pat. No. 5,427,773 discloses cationic photo-filter based on dimethyl amino benzamidopropyl moiety (Escalol HP 610) whereas U.S. Pat. No. 6,613,340 discloses cationic filters based on cinnamido moiety (TosyQuat) and in both cases, the hydrophobicity has been imparted to the molecule by the long hydrocarbon chain of twelve carbon atoms that is attached to a quaternary nitrogen. By virtue of being hydrophobic due to long alkyl chain and tosylate as counter anion, these quaternized UV absorbers do exhibit good substantivity to hair tresses but they suffer from two major disadvantages, namely, difficult to formulate and difficult to synthesize and thereby becoming cost-ineffective for the benefits derived.

The synthesis of quaternized UV absorbers with tosylate (U.S. Pat. No. 5,427,773 and U.S. Pat. No. 6,613,340) as counter ion is extremely complex. The synthesis involves a reaction of fatty alcohol tosylate with a tertiary amine containing an UV absorbing chromophore to create a quaternary ammonium center. Fatty alcohol tosylate required for this step in turn is synthesized by reacting tosyl chloride and fatty alcohol in the presence of tertiary amines in halogenated solvents like dichloromethane. Purification of fatty alkyl tosylate is essential (the salt of organic base formed when the base like triethylamine mops the HCl generated during tosylation) and these additional steps not only generate waste (disposal problem) but also result into significant reduction in overall yield thereby adding to the cost of product. The second disadvantage is the difficulty in formulating. p-methoxy cinnamidopropyl lauryl dimonium tosylate (U.S. Pat. No. 6,613,340) is a solid crystalline product and difficult to formulate particularly at higher percentage level since these are neither water-soluble nor oil-soluble and not easily dispersible. Dimethylamino PABA amidopropyl lauryl dimonium tosylate (Escalol HP 610) is mixed with propylene glycol stearate as process-aid. As a result of these limitations one does not come across marketed hair care formulations with Galaxy TosyQuat and Escalol HP 610 even though these molecules have been around for more than a decade. A few years ago Croda Inc USA, launched ChromAveil, a diesterquat that involves a multistep synthesis with dangerous chemicals like propylene oxide and dimethyl sulphate. Propylene oxide is reacted with N-methyl diethanol amine and the resultant adduct is then esterified by reacting terminal hydroxyl groups with two molecules of p-methoxy cinnamic acid. The diester, thus obtained, is then quaternized with dimethyl sulphate (U.S. Pat. No. 7,202,204). This commercial product, ChromAveil is sold as 70% solution in propane diol indicating apparent difficulty in formulating the quaternary product. Propoxylation confers the water-insolubility or water-dispersibility but it also results in branched chains that are difficult to biodegrade. It is well established fact that the branched alkyl chains are significantly difficult to biodegrade compared to linear alkyl chains. Also, dimethyl sulphate, the quaternizing agent used in the last step is one of most dangerous chemical health hazard known to mankind. It is a chemical weapon since it kills human beings instantaneously without giving any warning signs. Dimethyl sulphate is a likely carcinogen, mutagenic, poisonous, and corrosive. It is known to be volatile (inhalation hazard) and odorless hence it does not warn of the lethal concentration in air. This results in fetal situation without giving time to act. It is absorbed through the skin, mucous membrane and vapors damage eyes permanently. The other serious limitations of this product, ChromAveil, are color and strong odor and the presence of solvent.

Current survey of marketed products including new launches for hair color protectors (Euromonitor Data—'Ingredients Trends in Hair Care—Meeting Needs of 21$^{st}$ century', April 2011) show that the hair-care formulators seem to be continuing to use very inefficient water-soluble UV absorbers for creating formulations for protecting colored hair and from sun damage since there is no effective solution available.

In the absence of an effective alternative hair protector for color-fade and sun-damage, the formulators have been using inefficient and non-substantive or at best weakly substantive water-soluble UV absorbers and along with other conditioners like cetrimonium chloride, guar hydroxypropyl trimonium chloride, or behenyl trimethyl ammonium chloride. In view of the serious limitations of the quaternary UV absorbers that are available today there is a definite need to create a molecule that would not only protect the hair from UV damage and but would also repair the damage caused by chemical, heat or light treatment. Thus, there remains the need for an UV absorbing compound that would have adequate adhesion so that it not only protects hair from the damages but conditions without giving greasy feel.

OBJECT OF THE INVENTION

It is an object of the present invention to overcome the drawbacks of the prior art.

It is an object of the present invention to synthesize a quaternary ammonium conditioner for protecting hair and the applied color of hair (anti-fade) with UV absorbing moiety.

It is also an object of this invention to create a hair protector that would smoothen the damaged hair surface to the hair.

It is yet another object of the present invention to provide a cost-effective synthesis for the said hair color protector using 'green' chemistry and avoid toxic reagents that have been used in the prior art.

SUMMARY OF THE INVENTION

The present invention relates to a process for making the quaternary ammonium compound, p-methoxy cinnamidopropyl behenyl dimethyl ammonium chloride of Formula I wherein; R is a linear alkyl group with minimum of 80% behenyl (C 22) comprising the steps of:
  a) reacting p-methoxy cinnamoyl chloride (Formula III) with N,N-dimethyl aminopropylamine to give p-methoxy cinnamidopropyl dimethyl amine (Formula II) and
  b) quaternizing p-methoxy cinnamidopropyl dimethyl amine with behenyl chloride in aqueous medium to give the compound of Formula I.

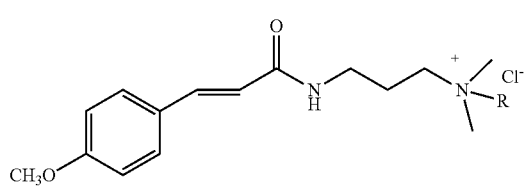

Formula I

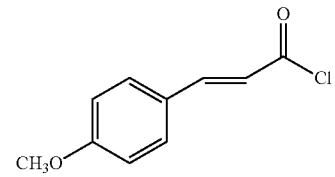

Formula III

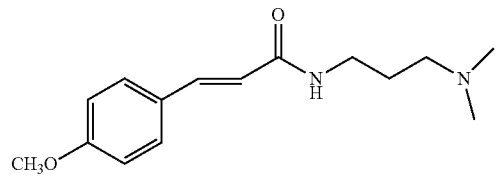

Formula II

BRIEF DESCRIPTION OF THE ACCOMPANYING DRAWINGS

FIG. 1: Results illustrating significant reduction of combing work observed, measured on Diastron tensile tester after one application through a shampoo application.

Figure 2:
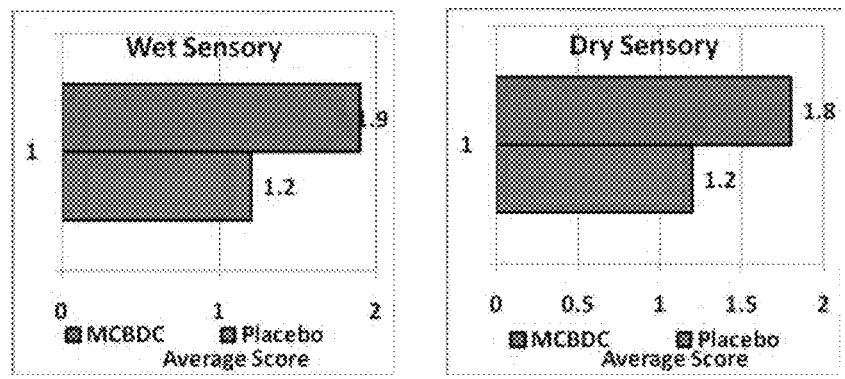

FIG. 2: Results illustrating hair strands treated with base shampoo and a shampoo containing MCBDC were examined for the sensorial evaluation.

Figure 3:
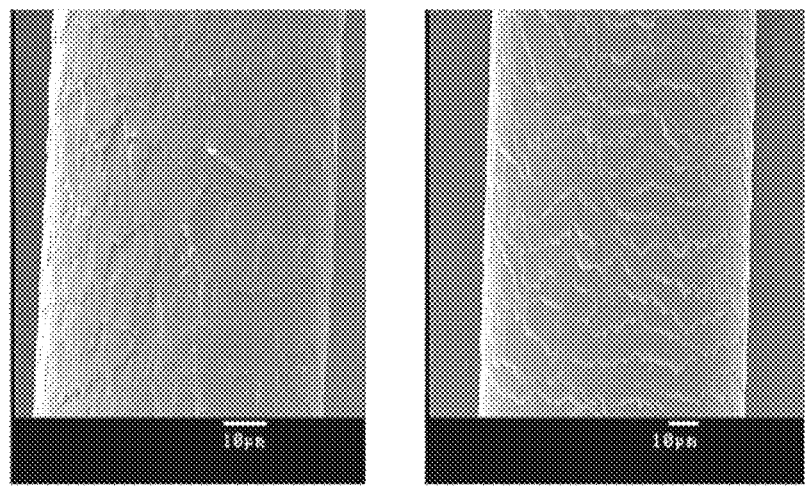

FIG. 3: Results illustrating smoothening of hair surface due to long alkyl chain of 22 carbons.

Figure 4:
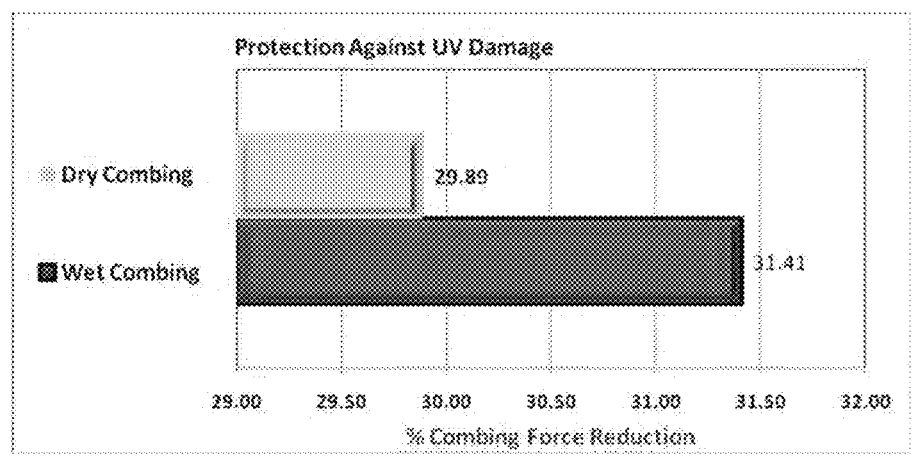

FIG. 4: Results illustrating 30% reduction in combing force using the test conditioner that had 2% of MCBDC indicating significant photo-protection.

Figure 5:
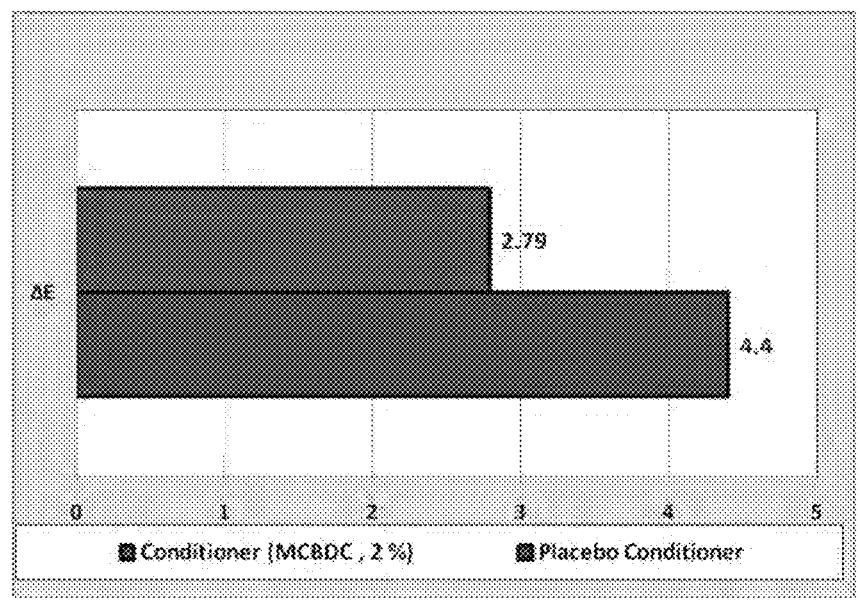

FIG. 5: Results illustrating small ΔE for the treated hair indicating retarding or arresting color fading.

Figure 6:
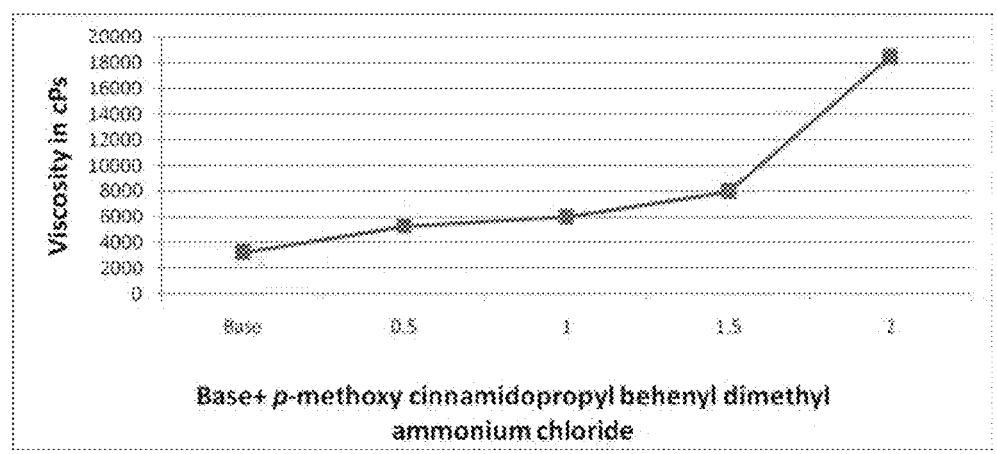

FIG. 6: Incorporation of MCBDC in the base formulation (salt content of 0.7% and viscosity of 3000 cps) ranging from 0.5% to 2.0% illustrating linear increase in viscosity.

DETAILED DESCRIPTION OF THE INVENTION

The substantive UV absorbing compound, p-methoxy cinnamidopropyl behenyl dimethyl ammonium chloride, Formula I, is prepared by a two step synthesis. The first step involves Schotten Baumann type of condensation between the p-methoxy cinnamoyl chloride (Formula III) and N,N-dimethyl aminopropylamine in aqueous medium to give the intermediate of p-methoxy cinnamidopropyl dimethyl amine (Formula II). And the second step is quaternization of tertiary nitrogen of p-methoxy cinnamidopropyl dimethyl amine (Formula II) with behenyl chloride in aqueous medium as shown in Scheme I Scheme I

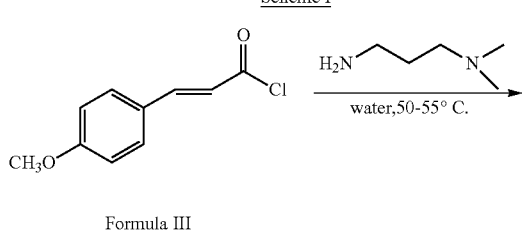

Formula III

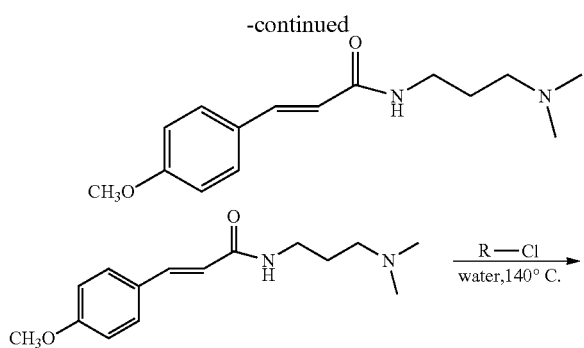

Formula II

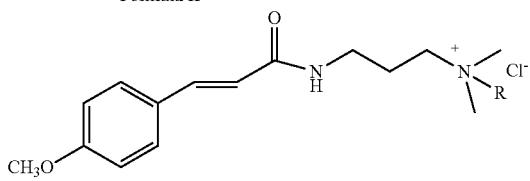

R=C$_{22}$H$_{45}$
Formula I

In the prior art ethyl or methyl esters of cinnamic acid have been reacted in a base catalyzed reaction with a diamine like N,N-dimethyl aminopropyl amine. The reactions conditions were extremely harsh with a temperature of 180 to 200° C. in special reactor that is capable of holding the high pressure generated due to the vaporization of excess of diamine and the lower alcohols generated as a result of amidification (U.S. Pat. No. 5,601,811 and U.S. Pat. No. 6,613,340). The limitations of the prior art are not just 1) severe temp and pressure conditions and 2) use of excess of a reactant and the recovery of the same excess reactant at the end of the reaction but it also suffers from a major disadvantage of the formation of undesirable side product. Under the extreme reaction conditions the primary amino group of the diamine reacts with 1,4 conjugated system in alkyl esters of cinnamic acid at the terminal carbon of the double bond instead of reacting at carbonyl carbon of ester group giving a saturated 'Michael Adduct'. In short, under the conditions described by the prior art the competing reactions (amidification versus Michael addition) are inevitable. Formation of 'Michael Adduct' results in the saturating of double bond and thereby loss of conjugation. Destruction of conjugation in this side product also loses the UV absorption power. The unavoidable formation of 'Michael Adduct' also entails purification of the product and thereby loss of the yield and additional cost of waste disposal.

The present invention describes reaction of cinnamoyl chloride at 50-55° C. without addition of any base catalyst or a base scavenger and in the most 'eco-friendly' solvent 'water' (first step of Scheme 1). The aqueous Schotten Baumann gives quantitative yield of the desired product and there no side reaction forming a Michael product. This step is described in the Example I of the experimental. The stoichiometric mole ratios of the reactants, p-methoxy cinnamoyl chloride to N,N-dimethyl aminopropylamine for aqueous Schotten Baumann reaction are 1.0:1.0 to 1.0:1.10. The primary amino group act as the nucleophile and the tertiary amino group acts like a base-scavenger to mop up the hydrogen chloride formed as a result of this condensation. The product is obtained as aqueous solution of hydrochloride of the cinnamidoamine. The p-methoxy cinnamidopropyl dimethyl amine is then liberated from its aqueous hydrochloride solution by basifying with caustic lye. Filtration of the precipitated solid, followed by washing and drying, results in near quantitative yield (over 90%) of the product. The aqueous reaction between another sunscreen acid, namely, N,N-dimethyl amino benzoyl chloride was successfully reacted with N,N-dimethyl propyl diamine to afford N,N-dimethyl amino benzamido propyl dimethyl amine in very high yield. Those who have reasonable knowledge of organic chemistry and Schotten Baumann reaction would easily understand that acid chloride of any sunscreen acid in the form of corresponding acid chloride can be reacted with such primary amines (e.g. N,N-dimethyl propyl diamine in this case) in water medium to give the corresponding UV absorbing amido amines.

The second step of the synthesis (Scheme 1) is carried in water medium, the most eco-friendly solvent, very conveniently by simply heating the stoichiometric quantities of the reactants, namely, p-methoxy cinnamidopropyl dimethyl amine (Formula II) and behenyl chloride in the presence of water. The quaternization of tertiary amines of this sort has been reported without any medium (U.S. Pat. No. 5,601,811, U.S. Pat. No. 7,205,436), however, the major disadvantage of this is that one has to resort to running the reaction at high temperatures to keep the reaction medium fluid particularly in the last stages when good amount of ionic compound is formed after 60-70% conversion. This resorting to higher temperature results in discoloration and absence of medium makes it difficult to achieve quantitative conversion and hence the purification of the product becomes necessary to get rid of unconverted starting materials. The quaternization of p-methoxy cinnamidopropyl dimethyl amine (Formula II) with behenyl chloride is reported by U.S. Pat. No. 7,147,866 in a protic solvent isopropyl alcohol. However, odorous lower alcohols or non odorous other protic alcohols or glycols either need to be removed and these add to overall cost of the process. The quantitative removal of solvents is quite cumbersome and often traces of solvent are left in the product. The present patent application teaches the quaternization in aqueous medium. The quaternization reaction is carried out conveniently with 20 to 80% water of the total reaction mass (step 2 of Scheme 1). Behenyl chloride that is employed for quaternizing p-methoxy cinnamidopropyl dimethyl amine (Formula II) can be 100% pure behenyl chloride or it can be a mixture of fatty acid chlorides with behenyl content of more than any other alkyl chain. Typically this invention relates to use of behenyl chloride with minimum of 80% by weight of C22 halide, docosanyl chloride. For the quaternization reaction in aqueous solution (step 2 of Scheme 1) ideal temperature range is 100 to 150° C. While doing it in a closed vessel, the air in the head space of reactor is driven off by nitrogen purging and the reactants are heated with good agitation at 120 to 140° C. The progress of the reaction is monitored by the reduction of p-methoxy cinnamidopropyl dimethyl amine. The Example 2 of the present invention reports the facile use of aqueous medium to get quantitative conversion and the resultant pasty product (30% solids, 70% water) at room temperature is easy to use. When quaternization of p-methoxy cinnamidopropyl dimethyl amine with behenyl chloride is carried in presence of 10% water at 150° C. the reaction is quantitative and the product results into a solid at room temperature. The product can be flaked or converted into needles/noodles by extrusion. (Example 3) For those who are skilled in the art of organic synthesis, it would be obvious that the aqueous quaternization reaction of sunscreen amido amines with alkyl halide with hydrocarbon chain of C6 (hexyl) to C20 (behenyl) is completely feasible. The quaternization reaction described in this patent application and similar reactions with other alkyl halides and sunscreen amidoamines could be due to the auto-catalysis of the quaternary UV absorbing surfactant emulsifying both hydrophobic and hydrophilic phases resulting into the quantitative formation of UV absorbing quaternary surfactants. The quaternary UV absorber of this patent application, p-methoxy cinnamidopropyl behenyl dimethyl ammonium chloride that is generated as aqueous paste ranging 30 to 50% active matter and nice flakable solid (90% active matter) at room temperature is conveniently analyzed by HPLC using reversed phase liquid chromatography. It is also analyzed by titrating against a cationic surfactant using mixed indicator as procedure given in the literature. (1) Milwidsky, B. M.; Gabriel, D. M.; Detergent analysis a handbook for cost-effective quality control; John Wiley & Sons, Inc., New York; 1982. 2) Cullum, D. C.; Introduction to surfactant analysis; Chapman & Hall; 1994)

The product, p-methoxy cinnamidopropyl behenyl dimethyl ammonium chloride (as described in Example 1 and 2) will be referred to as MCBDC hereafter in this section and in the experimental section.

MCBDC as an UV Absorber

MCDBC is obtained as practically odorless white paste and has solids content of 30% (Example 2). The product as such has absorbance (E 1%, 1 cm) of 130 at $\lambda$ max of 306 nm in ethanol.

Its molar extinction coefficient c is 28,000 when measured at same $\lambda$ max MCBDC as a Cationic Surface Active Agent This quaternized UV absorber of this patent application exhibits good surfactant properties. It reduces the surface tension of water from 72 Mn/m to 35 Mn/m at 1.0%, at 30° C., exhibiting excellent surface activity. It can be easily titrated with an anionic surfactant as a standard for two phase titration for the determination of active matter.

Zeta potential of 1% dispersion was found to be +47 mV when measured on Malvern instrument, Zetasizer Nano. This shows strong surface charge and hence the reason to be highly substantive to hair and skin surface. Also the high zeta potential ensures the stability of colloidal dispersions.

MCBDC as a Hair Conditioner p-Methoxy cinnamidopropyl behenyl dimethyl ammonium chloride (MCBDC) is about ten times more substantive to hair strands than normal water-soluble UV absorbers like Benzophenone-4. (This was established by using 0.5% aqueous solution/dispersion on hair tresses, MCDBC, 3217 µg/g of hair, and B-4 276 µg/g of hair). MCBDC also showed excellent deposition on hair through a shampoo formulation (in the presence of anionic surfactant) and a decent level of conditioning effect. When compared with a base placebo shampoo formulation (that did not have the quaternary MCBDC), the shampoo formulation containing 2.0% of MCBDC showed good conditioning and enhanced sensorial feel as described in 4. Significant reduction of combing work was observed when measured on Diastron tensile tester after one application through a shampoo application (Figure I). The hair strands that were treated with base shampoo and a shampoo containing MCBDC were examined for the sensorial evaluation and the findings have been summarized in Figure II. Thus, the significant reduction in combing work on both dry and wet hair and significant enhancement of sensory attributes is the result of deposition of the MCBDC as conditioner.

Excellent deposition due to strong cationic nature of MCDBC and thereby conditioning the hair tresses was also helpful in aligning the damaged cuticles of hair. The damaged hair were treated with simple dispersion of MCBDC (0.5%) for 30 seconds and rinsed off as described in 4. Upon examination under scanning electron microscope it was evident that the cuticles of the damaged tresses were realigned due to even spreading, highly substantive nature. This smoothening of hair surface is due to long alkyl chain of 22 carbons. (Figure III)

UV Protection Effect of MCBDC

The cationic nature of MCBDC makes it a highly substantive quaternized UV absorber. The p-methoxycinnamidopropyl moiety is one of the best highly conjugated moieties with high UV absorption power. Once deposited through a preparation like conditioner, MCBDC protects hair from the damage due to solar radiation. The solar damage to hair with breaking up of disulphide linkage in well established and it is also well established that blond hair are more susceptible. To measure the efficacy against UV light the double bleached European hair were treated with placebo (conditioner without MCBDC) and rinse-off conditioner (conditioner with MCBDC) and exposed to UV light as per the protocol described in Example 5. Measurement of combing work on Diastron Tensile tester subsequent to the exposure to UV radiation showed that compared to the control tresses (unexposed) and the placebo conditioner the test conditioner showed significant reduction in combing work indicating that the damage to hair tresses was much less in case of hair that were treated with the test conditioner containing 2% MCDBC. In both dry combing as well as wet combing the reduction in combing force is about 30% using the test conditioner that had 2% of MCBDC indicating significant photo-protection (IV)

Color Protection (Anti-Fade) Effect of MCBDC

Excellent UV absorption capacity coupled with good substantivity and good lubricating effect, MCBDC via rinse-off formulation helps in arresting the degradation of light sensitive color through rinse-off conditioners. Burgundy color was selected for dying the hair as described in the Example 6. Three sets of hair tresses were taken for the study and the control was not subjected to shampoo and conditioning cycles. The other two sets of dyed hair that were treated with ten cycles with shampoo/placebo conditioner/UV exposure and shampoo/test conditioner/UV exposure as described in experimental section, Example 6. The color fading, loss of color ($\Delta$E) was measured on Hunter L* a* b* color scale. The small $\Delta$E for the treated hair indicated retarding or arresting color fading that was applied to hair tresses (Figure V).

Viscosity Boosting Effect of MCBDC

MCBDC, a quaternized UV absorber of the present invention, seems to have a special advantage of boosting viscosity of a typical shampoo/skin cleanser type of formulations that are based on combination of anionic surfactant like sodium lauryl ether sulphate (SLES) and amphoteric/zwitterionic surfactant cocoamidopropyl betaine (CAPB). In such formulations betaines are often used as co-surfactants that also reduce the irritancy of anionic surfactants. For viscosity boosting almost invariably fatty alkanolamides are used, however, formulators ideally would like to avoid alkanolamides due to their implication in nitrosamine generation. MCBDC seems to offer a real significant viscosity boosting effect in these kinds of SLES-CAPB formulations (Example 7. The linear increase in the viscosity is depicted in Figure VI) and can be an alternative to controversial alkanolamides.

Antimicrobial Effect of MCBDC:

MCBDC in the form of 30% aqueous paste is self preserving. It was challenge tested with both Gram negative, Gram positive bacteria and yeast and mold by the standard challenge test protocol recommended by CTFA. The test organisms used were *P. aeruginosa, E. coli, S. aureus, Candida albicans* and *A. niger*.

The Advantages of p-Methoxy Cinnamidopropyl Behenyl Dimonium Chloride (MCBDC) are as Follows 1) It is highly substantive to hair, exhibits good conditioning effect. It aligns the damaged cuticles hair and thereby enhances the sensorial attribute of the formulation.
2) Protection to hair from UV radiation by virtue being substantive and an UV absorbing molecule.
3) Protection to the applied color (Anti-Fade) though regular hair care formulations like shampoo and conditioner.
4) High molecular weight (601 g/m), less penetration through the stratum corneum, safe as a personal care ingredient. Molecules with molecular weight of more than 500 Dalton are preferred since they do not permeate through skin.
5) MCBDC exhibits good surface activity since it has all the necessary features to be a cationic surfactant, the hydrophilic portion and hydrophobic portion. Drop in surface tension of water by 35 dynes demonstrated significant surface activity that can be exploited for forming cationic emulsions.
6) It forms paste in water at 30 to 50% concentration level. It gets easily dispersed in water and displays ease of incorporation in formulations.
7) In anionic-amphoteric surfactant cleaning systems MCBDC acts a substantial viscosity booster and it can provide a viable alternative to controversial alkanol amides. The overall process is very eco-friendly due to water as reaction medium and no waste disposal due to quantitative yields. The design of synthesis prevents formation of side products and thereby obviates the purification steps.
8) Aqueous solution (30%, Example 2) is self preserving.
9) Both steps synthesis are done in aqueous medium, Schotten Baumann chemistry as well as the quaternization of tertiary amine.

The invention will now be illustrated with the help of examples.

Examples 1 and 2 describe the process of manufacture of the compound of Formula I, p-methoxy cinnamidopropyl behenyl dimonium chloride. Example 3 describes synthesis of high active 90% active, p-methoxy cinnamidopropyl behenyl dimonium chloride as white solid flakes. Examples 4 to 8 illustrate the performance and the benefits through the formulations. The examples are by way of illustrations only and in no way restrict the scope of invention. Many changes and modifications can be made within the scope of the present invention without departing from the spirit thereof and the invention concluded all such modifications. A few formulations of hair care preparations incorporating the compound of the present invention, p-methoxy cinnamidopropyl behenyl dimonium chloride are given in Examples 9 to 12.

In this section p-methoxy cinnamidopropyl behenyl dimonium chloride will be referred to as MCBDC.

Example 1

Synthesis of p-Methoxy Cinnamido Propyl Dimethyl Amine

To a stirred solution of N,N-dimethyl aminopropylamine (60.6 g 0.58 gmol) in water (35 mL) at room temperature, under nitrogen blanket, molten p-methoxy cinnamoyl chloride (103 g, 0.52 gmol) was slowly added while maintaining the temperature between 50 to 55° C. over the period of 1 hr. The stirring was continued for additional two hours. At this stage water (20 mL) was added and the reaction mixture was cooled to 10° C. and was acidified with concentrated hydrochloric acid to pH of 2. The hydrochloride salt solution was filtered and the filtrate was basified using sodium hydroxide (45% solution) to the pH of 11. The product, p-methoxy cinnamidopropyl dimethyl amine precipitated as off white solid. It was filtered, washed with water and dried under vacuum at 40° C. to yield the amidoamine (126.0 g, 89%) as pale yellow colored solid (m.p. 92° C.).

Molar extinction coefficient, $\epsilon$, in methanol was found to be 24,224 at 290 nm.

IR in dichloromethane showed carbonyl stretching of amide at 1660 $cm^{-1}$ and NH stretching at 3300 $cm^{-1}$.

$^1$H NMR (300 MHz, CDCl$_3$): $\delta$ 1.73 (p, 2H, J=6.6 Hz), 2.2 (s, 6H), 2.42 (t, 2H, J=6.6 Hz), 3.45 (q, 2H, J=6.0 Hz), 3.81 (s, 3H), 6.27 (d, 1H, J=15.6 Hz), 6.86 (d, 2H, J=8.7 Hz), 7.43 (d, 2H, J=8.7 Hz), 7.53 (d, 1H, J=15.6 Hz).

Example 2

Synthesis of p-Methoxy Cinnamidopropyl Behenyl Dimethyl Ammonium Chloride (MCBDC)

A mixture of p-methoxy cinnamido propyl dimethyl amine (120 g, 0.45 gmol), behenyl chloride (155 g, 0.45 gmol) in water (645 mL) was heated in a stainless steel pressure reactor after purging the vessel with nitrogen for half hour and was filled with nitrogen (1 kg/cm$^2$). The reaction mass was stirred at 140° C. for four hours and the progress of the reaction was monitored by analyzing the free methoxy cinnamido propyl dimethyl amine. Reaction was continued for additional 4 hr after the free amidoamine of less than 0.5% was achieved. The reaction mass was cooled to 70° C. and drained in the container to yield the quaternary product (900 g) as off-white paste. (solids content 30.2%, chloride ion content 1.7%, free cinnamidoamine 0.2%)

IR showed carbonyl stretching of amide at 1659 $cm^{-1}$ and NH stretching at 3377 $cm^{-1}$, CH stretch at 2917 and 2849 $cm^{-1}$ The white pasty mass that is practically odorless had E1% 1 cm of 130 at $\lambda$ max 306 nm in EtOH.

HPLC details: MCBDC is conveniently analyzed by high pressure liquid chromatography using reversed phase technique (column: RP-18 octadecyl bonded), mobile phase: water acetonitrile (gradient with a flow of one mL per minute) and detection at 306 nm.

Example 3

Synthesis of p-Methoxy Cinnamidopropyl Behenyl Dimethyl Ammonium Chloride (MCBDC)

A mixture of p-methoxy cinnamido propyl dimethyl amine (100 g, 0.38 gmol), behenyl chloride (130 g, 0.38 gmol) in water (25 mL) was heated in a stainless steel pressure reactor after purging the vessel with nitrogen for half hour and was filled with nitrogen (1 kg/cm²). The reaction mass was stirred at 150° C. for eight hours and the progress of the reaction was monitored by analyzing the free methoxy cinnamido propyl dimethyl amine. Reaction was continued for additional 4 hr after the free amidoamine of less than 1.0% was achieved. The reaction molten reaction mass flaked by evenly spreading in a steel tray and was scrapped of as fine solid flakes. The yield was quantitative with anionic activity of 89% by two phase titration against standard anionic surfactant.

Example 4

Conditioning Effect Through Shampoo Formulations (Measurement of Combing Work Reduction and Sensory Evaluation)

A typical placebo shampoo base was prepared with sodium lauryl ether sulphate (12%), cocoamidopropyl betaine (4%), EDTA disodium salt (0.1%), preservative (1%, phenoxy ethanol containing four parabens) and rest deionized water. Another shampoo formulation was prepared where 2% water was replaced by methoxy cinnamidopropyl behenyl dimonium chloride (MCBDC). All ingredients were mixed using a Silverson homogenizer thoroughly till a uniform homogeneous mixture was formed. The viscosity of placebo shampoo was found to be 3000.cps and the viscosity of the shampoo containing with cationic conditioner, MCBDC, was found to be 18,000 cps

| INCI Names | Placebo | Shampoo with MCBDC |
|---|---|---|
| Aqua | To make 100.0 | To make 100.0 |
| Sodium lauryl ether sulphate | 10.00 | 10.00 |
| Cocamido propyl betaine | 5.0 | 5.0 |
| Methoxy cinnamidopropyl behenyl dimonium chloride | | 2.0 |
| Phenoxyethanol and parabens | 1.0 | 1.0 |

Double bleached European hair were treated (150 cm long, 1.5 g) with 10% SLES and dried. Six such hair tresses were then again treated with placebo shampoo and with the shampoo containing MCBDC for one minute and were rinsed off with warm water (40° C.). The combing resistance was then measured in terms of the force required to pull a comb through a tress of a hair. Each tress was combed on the Diastron tensile tester (MTT 175). Experimental conditions maintained are a) temperature of 22° C. and b) relative humidity of 60%.

Hard rubber comb was used for the analysis. Ten combing strokes were conducted for each tress and averaged to obtain a representative value. After the average combing force was determined for each wet tress, the tresses were allowed to dry at room temperature for 18 h before average combing force was measured on the dry tresses. In the similar manner both wet and dry combing force was measured for the hair tress before the treatment with a shampoo with MCBDC. The test results are summarized as % combing reduction for the test shampoo formulations against the untreated tresses. (Figure I)

The hair tresses treated with the shampoo containing MCBDC (2%) showed significant reduction in the combing force in vitro measurement From the above results (Figure I), 51.08% in wet combing and 19.40% in dry combing respectively as compared to placebo shampoo. Sensory Evaluation of shampooed hair: The subjective evaluation was conducted by the panel of 10. The evaluator scored tresses of the scale of 1 to 2. The average of these results are summarized in graphs of Figure II Aligning of Disrupted Hair Cuticles: Scanning Electron Microscopy.

Asian double bleached hair that showed severe damage to cuticles on examination with scanning electron microscopy were treated with 0.5% dispersion in water for one minute and then rinsed off with water for 30 seconds. Examination under scanning electron microscope revealed that the damaged hair cuticles were aligned very nicely. (Figure III) This was also very evident from the subjective sensory evaluation.

Example 5

Hair Protection Against UV Induced Damage Through Rinse-Off Conditioner

The rinse-off conditioners (placebo and with MCBDC) with the following compositions were made. Double bleached European hair were shampooed with the placebo shampoo of Example 4 and conditioned according to the following protocol. The details of UV chamber and exposure conditions are given below. The difference in wet and dry combing force after application of placebo conditioner and with MCBDC and UV exposure is measured by Diastron MTT 175.

| INCI Names | Placebo | With MCBDC |
|---|---|---|
| Aqua | To make 100.0 | To make 100.0 |
| Hydroxy ethyl cellulose | 0.5 | 0.5 |
| Cetostearyl alcohol | 3.0 | 3.0 |
| | | 2.0 |
| Phenoxyethanol and parabens | 0.5 | 0.5 |

Applicatory Protocol

Placebo shampoo of Example 4 was applied for 1 minute to European hair and rinsed the tresses with water for one minute 25° C. with controlled finger movements. This was followed by conditioner application for one minute application time, one minute contact time and one and half minute for rinsing off with warm water (40° C.).

UV Exposure

Treated hair tresses were exposed to UV radiation with the help of UV lamp for 48 hours. UV exposed hair tresses were then subjected to combing force evaluation on Diastron tensile tester.

The procedure in detail: Photo-protection efficacy of a conditioner with MCBDC was determined by shampooing the hair traces (150 mm long and 1.5 g European double bleached) and conditioning as per the protocol described above. Two tresses per treatment were used. The treated tresses were irradiated with UV chamber which is equipped with two tubes emitting UV light in short UV (254 nm) and long UV 315-400 nm) regions. Sankyo Denki G8TS tube with UV output of 2.5 W was used as short UV light source while Sankyo Denki F8T5BLB backlight—blue tube with UV output of 1.4 W was used as long UV light source. Washing and UV exposure was given in the following sequence for 50 h. UV exposed tresses were washed with isopropanol to remove the quaternary followed by combing force measurement on Diastron Tensile Tester (MTT 175). The findings are summarized as % combing force reduction of tresses treated with conditioner containing MCBDC as compared to the tresses treated with the placebo conditioner.

Figure IV shows that in both dry as well as wet combing the reduction in combing force is about 30% in the conditioner that had 2.0% of MCBDC indicating significant photoprotection.

Example 6 p-Methoxy Cinnamidopropyl Behenyl Dimonium Chloride (MCBDC) as Hair Color Protector Through a Rinse-Off Conditioner The conditioner formulations (Placebo and with MCBDC) were prepared as described in Example 5. The Indian bleached hair tresses were shampooed by the placebo shampoo of Example 4. They were dyed using L'Oreal's Burgundy color as per the protocol described by the dye manufacturer.

Hair coloring (hair dyeing) process is performed as recommended by the marketed product. The color and the developer were mixed in ratio of 1:1 and shampooed hair tresses were treated with the same. The color and developer mixture was applied uniformly to the hair tresses and covered with the aluminum foil for twenty minutes. After this the hair tresses were washed with warm water. The colored hair tresses were divided into three groups, namely, control (colored and treated with placebo shampoo), placebo (colored and treated with placebo shampoo and a rinse off conditioner) and treated (colored and treated with placebo shampoo and conditioner with MCBDC). The 'Placebo' and 'Treated' hair tresses were exposed to UV radiation, total exposure of five hours through total to washing cycles comprising, shampooing, conditioning, rinsing and UV exposure of 30 mins at time using the equipment described in Example 5. The fading of color of the sets of hair tresses, Control, Placebo and Treated was measured on the Hunter instrument, Labscan XE spectrophotometer. The total color loss ($\Delta E$) is assessed by the change in L* a* b* scale using the equation $\Delta E=[(\Delta L)^2+(\Delta a)^2+(\Delta b)^2]^{1/2}$.

The results are summarized in Fig V.

Lower $\Delta E$ in case of the 'treated' set as compared to the 'placebo' set when compared with the 'control' showed that the significant anti-fade activity of the rinse-off conditioner with p-methoxy cinnamidopropyl behenyl dimonium chloride, MCBDC.

Example 7

Viscosity Boosting Property of MCBDC in a Shampoo Formulation

The base shampoo based on sodium lauryl ether sulphate (2EO) and cocoamidopropyl betaine was prepared as described in Example 4. Incorporation of MCBDC in the base formulation (salt content of 0.7% and viscosity of 3000 cps) ranging from 0.5% to 2.0% showed linear increase in viscosity (Figure VI) of the shampoo formulation when measured on Brookfield viscometer spindle No 4, 12 rpm, at 25° C.

Example 8

Challenge Test Performed on Aqueous Paste (30%) of p-Methoxy Cinnamidopropyl Behenyl Dimonium Chloride (MCBDC)

Following strains of Gram positive, Gram negative bacteria and yeast and mold were used for the challenge test. *Staphylococcus aureus* ATCC 653, *Escherichia coli* ATCC 8739, *Pseudomonas aeruginosa* ATCC 15442, *Candida albicans* ATCC 10231, and *Aspergillus niger* ATCC 16404.

The test is conducted in the six sterile containers each containing a fix equal amount of test sample. Each container was inoculated with a 1% of standardized Inoculum of the microorganism.

The initial concentration of the viable microorganism in each test preparation is estimated based on the concentration of microorganism in each of the standardized Inoculum as determined by the plate count method.

Each container is incubated at 25° C. The aliquot of sample of each container is removed at appropriate intervals of time 0 day, 24 hrs, 48 hrs, and 7 days, 14 days, 21 days and 28 days. The results are summarized in the following table.

| TVC in cfu/gm | S. aureus | E. coli | Ps. Aeruginosa | C. albicans | Asp. niger |
|---|---|---|---|---|---|
| 0 hr | $3 \times 10^6$ | $0.41 \times 10^4$ | $0.43 \times 10^5$ | $0.6 \times 10^3$ | $0.78 \times 10^5$ |
| 24 hr | <10 | <10 | $4.16 \times 10^4$ | <10 | $1.16 \times 10^1$ |
| 48 hr | <10 | <10 | $4.16 \times 10^4$ | <10 | $2.03 \times 10^2$ |
| 7 days | <10 | <10 | <10 | <10 | <10 |
| 14 days | <10 | <10 | <10 | <10 | <10 |
| 21 days | <10 | <10 | <10 | <10 | <10 |
| 28 days | <10 | <10 | <10 | <10 | <10 |

Carbopol Ultrez 20 is an acrylate polymer available for Lubrizol. Silicone DC 2088 is available with Dow Corning. Quinoa ProEx is hydrolyzate of Quinoa and available from Tri-K Industries Inc. Galaxy SunBeat (methoxy cinnamidopropyl hydroxyl sultaine) is a water-soluble UV absorber available from Galaxy Surfactants Ltd. Phenoxy ethanol with five parabens (Galgurard NK1/NK2) is available with Galaxy Surfactants Ltd.

Example 9

Color Protection Shampoo

| Ingredients | % (w/w) |
|---|---|
| Phase A | |
| Deionized water | To make 100.0 |
| Polyquaternium 10 | 00.20 |
| Carbopol Ultrez - 20 | 00.10 |
| Phase B | |
| Sodium lauryl ether sulphate (28%) | 30.00 |
| Sodium cocoyl sarcosinate (30%) | 10.00 |
| Cocoamidopropyl betaine (35%) | 05.00 |
| MCBDC (methoxy cinnamidopropyl behenyl dimonium chloride) (100%)s | 2.00 |
| PEG 150 distearate | 01.50 |
| Ethylene glycol distearate | 02.00 |
| Phase C | |
| DC 2088 | 02.00 |
| Polyquaternium 7 | 02.00 |
| Quinoa ProEx | 01.00 |
| Galaxy SunBeat | 05.00 |
| EDTA Na$_2$ salt | 00.10 |
| Phenoxy ethanol with parabens | 00.50 |

Procedure:

Disperse Polyquaternium 10 in water. Heat all the ingredients of phase A to 75° C. under slow stirring. Add phase B to phase A and mix until homogeneous. Cool down to room temperature and add phase C, stir until uniform. Adjust pH of the final formulation with 50% citric acid. Blend in fragrance and color.

Example 10

Sulfate-Free Shampoo

| Ingredients | % (w/w) |
|---|---|
| Phase A | |
| Deionized water | To make 100.0 |
| Gaur hydroxypropyl trimmonium chloride | 00.20 |
| Phase B | |
| Sodium cocoyl glycinate | 05.00 |
| Sodium lauroyl sarcosinate | 10.00 |
| Alkyl polyglucoside (C8/C10) | 10.00 |
| Sodium cocoyl taurate | 15.00 |
| Cocamidopropyl betaine | 10.00 |
| MCBDC | 06.66 |
| PEG 150 distearate | 02.50 |
| Phase C | |
| Dimethicone | 02.00 |
| Polyquaternium - 7 | 02.00 |
| Hydrolyzed quinoa protein | 01.00 |
| Galaxy SunBeat | 05.00 |
| EDTA disodium salt | 00.10 |
| Phenoxy ethanol with parabens | 00.50 |

Procedure: Disperse Polyquaternium 10 in water. Heat all the ingredients of phase A to 75° C. under slow stirring. Add phase B and mix until homogenous. Cool down to room temperature and add phase C, stir until uniform. Adjust pH of the final formulation with 50% citric acid. Blend in fragrance and color.

Example 11

Hair Conditioner

| Components | Range (% w/w) |
|---|---|
| Phase A | |
| Water | 47.44 |
| Hydroxy ethyl cellulose | 01.20 |
| Glycerin | 10.00 |
| EDTA Na$_2$ salt | 00.10 |
| MCBDC | 06.66 |
| Phase B | |
| Liquid paraffin | 35.00 |
| Stearic acid | 01.00 |
| Cetearyl alcohol | 03.50 |
| Cyclomethicone | 01.00 |
| Phase C | |
| PEG-7 glyceryl cocoate | 2.00 |
| Cocodimonium hydroxypropyl hydrolyzed keratin | 0.50 |
| Polyquaternium - 7 | 2.00 |
| Phenoxy ethanol with parabens | 0.10 |

Procedure: Disperse hydroxyethyl cellulose in water. Heat all the ingredients of phase A to 75° C. under slow stirring. Add phase B to phase A and mix until homogeneous. Cool down to room temperature and add phase C and stir until uniform. Adjust pH of the final formulation with 50% citric acid. Blend in fragrance and color.

Example 12

Hair Serum

| Components | Range (% w/w) |
|---|---|
| Phase A | |
| Water (Aqua) | To make 100.00 |
| Hydroxy methyl propyl Cellulose | 00.40 |
| Polyquaternium - 10 | 00.20 |
| PEG-12 dimethicone | 00.50 |
| *Aloe vera* gel | 01.00 |
| Phase B | |
| Glycerin | 03.00 |
| MCBDC | 02.00 |
| EDTA Na$_2$ salt | 00.10 |
| Galaxy SunBeat | 05.00 |
| Phase C | |
| Cyclomethicone | 02.00 |
| PEG-7 glyceryl cocoate | 02.00 |
| Polyquaternium - 7 | 02.00 |
| Phenoxy ethanol with parabens | 00.10 |

Procedure:

Disperse hydroxy propyl methyl cellulose in water. Heat all the ingredients of phase A to 75° C. under slow stirring. Add phase B and mix until homogenous. Cool down to room temperature and add phase C, stir until uniform. Adjust pH of the final formulation with 50% citric acid. Blend in fragrance and color.

This invention may be embodied in other forms or carried out in other ways without departing from the spirit or essential characteristics thereof. The present embodiments are therefore to be considered as in all respects illustrative and not restrictive, the scope of the invention being indicated by the appended claims, and all changes which come within the meaning and range of equivalency are intended to be embraced therein.

We claim:

1. A process for making the quaternary ammonium compound, p-methoxy cinnamidopropyl behenyl dimethyl ammonium chloride of Formula I, wherein R is a linear alkyl group with minimum of 80% by wt. behenyl (C 22) said process comprising the steps of:
   a) reacting p-methoxy cinnamoyl chloride (Formula III) with N,N-dimethyl aminopropylamine in aqueous medium to give p-methoxy cinnamidopropyl dimethyl amine (Formula II) and
   b) quaternizing p-methoxy cinnamidopropyl dimethyl amine with behenyl chloride at temperature of 140° C.-150° C. and pressure of 1 Kg/cm$^2$, for 8-12 hours, in aqueous medium to give the compound of Formula I

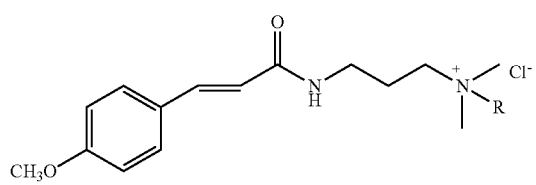

Formula I

-continued

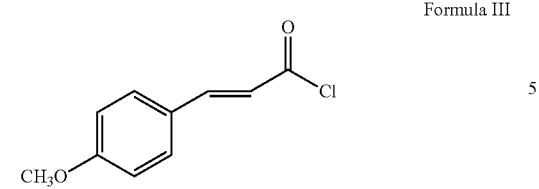
Formula III

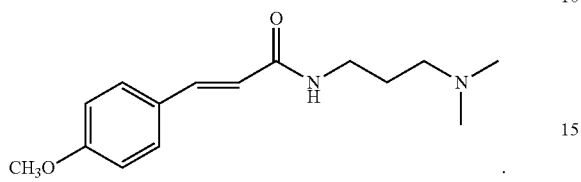
Formula II

2. The process for making the quaternary ammonium compound as claimed in claim 1, wherein the composition of behenyl chloride used for quaternizing p-methoxy cinnamidopropyl dimethyl amine of Formula II, has behenyl chloride (C22) content higher than other two other alkyl chlorides, wherein the two other alkyl chlorides are arachidyl chloride (C20) and stearyl chloride (C18).

* * * * *